United States Patent
Venturini

(10) Patent No.: US 10,631,896 B2
(45) Date of Patent: Apr. 28, 2020

(54) ELONGATED PIN FOR AN EXTERNAL MODULAR FIXATION SYSTEM FOR TEMPORARY AND/OR PERMANENT FIXATION APPLICATIONS AND EXTERNAL MODULAR FIXATION SYSTEM

(71) Applicant: Orthofix S.r.l., Bussolengo (Verona) (IT)

(72) Inventor: Daniele Venturini, Povegliano Veronese (IT)

(73) Assignee: Orthofix S.r.l., Bussolengo (Verona) (IT)

( * ) Notice: Subject to any disclaimer, the term of this patent is extended or adjusted under 35 U.S.C. 154(b) by 355 days.

(21) Appl. No.: 14/417,051

(22) PCT Filed: Jul. 4, 2013

(86) PCT No.: PCT/EP2013/001965
§ 371 (c)(1),
(2) Date: Jan. 23, 2015

(87) PCT Pub. No.: WO2014/015942
PCT Pub. Date: Jan. 30, 2014

(65) Prior Publication Data
US 2015/0209081 A1    Jul. 30, 2015

(30) Foreign Application Priority Data

Jul. 25, 2012   (EP) .................................... 12177909

(51) Int. Cl.
*A61B 17/64* (2006.01)
*A61B 17/66* (2006.01)
*A61B 17/86* (2006.01)

(52) U.S. Cl.
CPC ........ *A61B 17/6458* (2013.01); *A61B 17/645* (2013.01); *A61B 17/6466* (2013.01);
(Continued)

(58) Field of Classification Search
CPC .......... A61B 17/58–66; A61B 17/8897; A61B 17/86; A61B 17/848; A61B 17/645;
(Continued)

(56) References Cited

U.S. PATENT DOCUMENTS 1,960,892 A * 5/1934 Boever ................. A61B 17/60
606/102
3,915,162 A * 10/1975 Miller ................. A61B 17/8625
606/102

(Continued)

FOREIGN PATENT DOCUMENTS

| EP | 0 557 899 A1 | 9/1993 |
| EP | 1 042 989 B1 | 3/2004 |

(Continued)

OTHER PUBLICATIONS

International Search Report issued in connection with PCT/EP2013/001965.
(Continued)

*Primary Examiner* — Jacqueline T Johanas
(74) *Attorney, Agent, or Firm* — Akerman LLP

(57) ABSTRACT

The invention relates to an elongated pin (2) for an external modular fixation system for temporary and/or permanent fixation applications to treat bone fractures and to connect two or more bone fragments to each other, comprising an elongated stem (3) extending along a longitudinal axis with a first end portion (4) and an opposite second end portion (5), said first end portion (4) having a tip for the insertion of the first end portion (4) into a bone, wherein said first end portion (4) has a conical shape with an external thread, forming a conical threaded end portion, the extension of said conical threaded end portion along the longitudinal axis being determined by the depth of penetration of the conical end portion limited to only the cortical portion of the bone.

9 Claims, 9 Drawing Sheets

(52) U.S. Cl.
CPC .......... *A61B 17/66* (2013.01); *A61B 17/8625* (2013.01); *A61B 17/8635* (2013.01)

(58) Field of Classification Search
CPC . A61B 17/6458; A61B 17/6466; A61B 17/66; A61B 17/8625; A61B 17/8635
USPC .......................................... 606/311, 312, 318
See application file for complete search history.

(56) References Cited

U.S. PATENT DOCUMENTS

| | | | | |
|---|---|---|---|---|
| 4,127,119 | A * | 11/1978 | Kronner | A61B 17/62 606/56 |
| 4,463,753 | A * | 8/1984 | Gustilo | A61B 17/863 411/386 |
| RE31,809 | E * | 1/1985 | Danieletto | A61B 17/6458 403/137 |
| 4,548,199 | A * | 10/1985 | Agee | A61B 17/1782 606/55 |
| 4,942,872 | A * | 7/1990 | Jawish | A61B 17/60 606/57 |
| 5,064,425 | A * | 11/1991 | Branemark | A61C 8/0024 606/304 |
| 5,300,076 | A * | 4/1994 | Leriche | A61B 17/8635 411/395 |
| 5,593,410 | A * | 1/1997 | Vrespa | A61B 17/863 606/312 |
| 5,690,633 | A * | 11/1997 | Taylor | A61B 17/8605 606/54 |
| 5,863,292 | A * | 1/1999 | Tosic | A61B 17/62 606/56 |
| 5,943,258 | A * | 8/1999 | Houston | G11C 11/412 257/E21.661 |
| 6,099,529 | A * | 8/2000 | Gertzman | A61B 17/8605 606/309 |
| 6,159,210 | A * | 12/2000 | Voor | A61B 17/6433 606/56 |
| 6,238,417 | B1 * | 5/2001 | Cole | A61B 17/8047 606/213 |
| 6,277,119 | B1 * | 8/2001 | Walulik | A61B 17/645 606/56 |
| 6,423,061 | B1 * | 7/2002 | Bryant | A61B 17/152 606/54 |
| 6,423,062 | B2 * | 7/2002 | Enayati | A61B 17/8635 606/318 |
| 6,585,736 | B2 * | 7/2003 | Hajianpour | A61B 17/60 606/57 |
| 6,699,251 | B1 * | 3/2004 | Venturini | A61B 17/8605 606/318 |
| 6,949,100 | B1 * | 9/2005 | Venturini | A61B 17/8625 606/318 |
| 7,153,302 | B1 * | 12/2006 | Hajianpour | A61B 17/60 606/57 |
| 7,169,149 | B1 * | 1/2007 | Hajianpour | A61B 17/72 606/54 |
| 7,731,738 | B2 * | 6/2010 | Jackson | A61B 17/8635 606/300 |
| 7,758,582 | B2 * | 7/2010 | Ferrante | A61B 17/6466 606/96 |
| 8,083,740 | B2 * | 12/2011 | Eslami | A61B 17/6475 606/56 |
| 8,268,530 | B2 * | 9/2012 | Utsumi | C07D 317/54 430/270.1 |
| 8,372,125 | B2 * | 2/2013 | Hansson | A61B 17/60 606/301 |
| 8,915,914 | B2 * | 12/2014 | Venturini | A61B 17/64 606/54 |
| 9,060,809 | B2 * | 6/2015 | Tipirneni | A61B 17/685 |
| 2001/0034520 | A1 * | 10/2001 | Enayati | A61B 17/8635 606/59 |
| 2003/0004518 | A1 * | 1/2003 | Perren | A61B 5/1077 606/102 |
| 2003/0040751 | A1 * | 2/2003 | Weil, Sr. | A61B 17/863 606/311 |
| 2003/0153910 | A1 * | 8/2003 | Janowski | A61B 17/645 606/56 |
| 2004/0167519 | A1 * | 8/2004 | Weiner | A61B 17/8665 606/60 |
| 2004/0167530 | A1 * | 8/2004 | Hamel | A61B 17/66 606/86 R |
| 2005/0043730 | A1 * | 2/2005 | Janowski | A61B 17/645 606/56 |
| 2005/0085754 | A1 | 4/2005 | Werding et al. | |
| 2007/0173837 | A1 * | 7/2007 | Chan | A61B 17/66 606/63 |
| 2007/0255280 | A1 * | 11/2007 | Austin | A61B 17/6416 606/54 |
| 2008/0221574 | A1 * | 9/2008 | Cavallazzi | A61B 17/1739 606/62 |
| 2008/0262555 | A1 * | 10/2008 | Assell | A61B 17/1615 606/301 |
| 2008/0275510 | A1 * | 11/2008 | Schonhardt | A61B 17/8047 606/286 |
| 2009/0099584 | A1 * | 4/2009 | Piferi | A61B 17/16 606/180 |
| 2009/0118733 | A1 * | 5/2009 | Orsak | A61B 17/60 606/60 |
| 2009/0138053 | A1 * | 5/2009 | Assell | A61F 2/4405 606/301 |
| 2009/0187194 | A1 * | 7/2009 | Hamada | A61B 17/7001 606/104 |
| 2010/0211118 | A1 * | 8/2010 | Christen | A61B 17/8635 606/312 |
| 2011/0004211 | A1 * | 1/2011 | Matityahu | A61B 17/6408 606/59 |
| 2011/0112533 | A1 * | 5/2011 | Venturini | A61B 17/6466 606/54 |
| 2011/0125198 | A1 | 5/2011 | Griffin | |
| 2011/0125199 | A1 * | 5/2011 | Griffin | A61B 17/8625 606/312 |
| 2011/0264149 | A1 | 10/2011 | Pappalardo et al. | |
| 2011/0295252 | A1 * | 12/2011 | Tipirneni | A61B 17/683 606/62 |
| 2012/0029575 | A1 * | 2/2012 | Orsak | A61B 17/60 606/286 |
| 2013/0172888 | A1 * | 7/2013 | Necuze | A61B 17/66 606/59 |
| 2013/0325076 | A1 * | 12/2013 | Palmer | A61B 17/1739 606/318 |
| 2014/0031822 | A1 * | 1/2014 | Venturini | A61B 17/64 606/59 |

FOREIGN PATENT DOCUMENTS

| | | |
|---|---|---|
| EP | 1 284 666 B1 | 1/2007 |
| EP | 2 319 436 A1 | 5/2011 |

OTHER PUBLICATIONS

International Preliminary Report on Patentability issued in connection with PCT/EP2013/001965.

* cited by examiner

ELONGATED PIN FOR AN EXTERNAL MODULAR FIXATION SYSTEM FOR TEMPORARY AND/OR PERMANENT FIXATION APPLICATIONS AND EXTERNAL MODULAR FIXATION SYSTEM

This application is a national phase of PCT/EP2013/001965, filed Jul. 4, 2013, and claims priority to EP 12177909.4, filed Jul. 25, 2012, the entire contents of both of which are hereby incorporated by reference.

TECHNICAL FIELD

The present invention relates to an elongated pin for an external modular fixation system for temporary and/or permanent fixation applications and to an external modular fixation system using said pin.

PRIOR ART

External fixation systems are widely used to treat bone fractures and to connect two or more bone fragments to each other. Known systems employ bone screws, pins and/or wires that are inserted into the bones and that use external structural elements such as fixation clamps, fixation rods, bars and rings to provide a rigid frame structure to hold the bone fragments in an intended place until a permanent healing.

In other treatments local conditions surrounding the individual fracture may occasionally preclude permanent fracture fixation, or the fracture may be concomitant with other fractures in an overall injury pattern that will require lengthy surgery before permanent fixation can be completed or before other fixation devices may be applied.

Even in such cases, however, some or all of the fractures can be treated by external fixation systems that are specifically designed for temporary fixation and that can therefore be considered temporary systems, for instance as disclosed in EP 2 319 436 for the same Applicant.

In any case, it is very important that at the end of the primary treatment each long bone has a stable fixation and that each fracture is contained in a stable manner.

In this technical field there are also many fixation systems that are mainly used as permanent fixation systems to provide bone fracture healing, for instance the system as disclosed in EP 1 284 666 for the same Applicant.

Generally speaking temporary fixation systems are lighter and simpler but also less stable when compared to known permanent external fixation systems and manufacturers provide different catalogue products to clearly identify the two different fields of application and their corresponding products. Moreover, temporary and permanent external fixation systems can often be differentiated by the shape and structure of their respective clamps.

Still in general terms, permanent external fixation systems and devices provide a high degree of stiffness and stability to control forces of lateral bending and torque during the treatment.

This stiffness and stability derive in part from the alignment of the bars of the fixator along the lengthwise axis of the bone that is being treated, partly through the inherent rigidity of the system and partly from the number of screws and bone interfaces.

It would be highly desirable to have the possibility to use an external fixation system combining the characteristics of simplicity and lightness of a temporary fixation system and the characteristics of robustness and stability of a permanent fixation system, but so far all methods known from prior art solutions have not produced efficient results.

The technical problem of the present invention is that of providing an elongated pin for an external modular fixation system for temporary and/or permanent fixation applications and an external modular fixation system using said pin, to offer stable and robust fixation of bone fragments while keeping the entire system extremely light to avoid problems of infection, while ensuring at the same time that the application of the system by a surgeon is straightforward.

Another aim of the present invention is that of providing an elongated pin for a modular fixation system that can be driven into the bone without the use of bone screws, which makes it possible to limit the gripping action to just the cortical portion of the fractured bone.

Another purpose of the present invention is that of allowing the same fixation system to be used also for bone lengthening procedures in preadolescent children or in adults.

SUMMARY OF THE INVENTION

The basic idea of the present invention is based on providing an elongated pin or rod with a threaded end that is implanted into only the cortical portion of the fractured bone and fixed to a plate clamp element; a group of at least three of such pins is fixed on a single clamp plate element and the pins are implanted according to different, non-coplanar directions to create a strong gripping action without reaching or damaging the medullary canal.

According to the above inventive idea the technical problem is solved by an elongated pin for an external modular fixation system for temporary and/or permanent fixation applications for the treatment of bone fractures according to claim 1 of the present invention.

The invention further relates to an external modular fixation system for temporary and/or permanent fixation applications for the treatment of bone fractures and connecting two or more bone fragments to each other according to claim 7.

The dependent claims outline preferred and particularly advantageous embodiments of the elongated pin and of the apparatus respectively, according to the invention.

Further features and advantages will be apparent from the following description of some preferred, but not exclusive, embodiments of the present invention, with reference to the attached drawings, given by way of non-limiting examples.

DETAILED DESCRIPTION

Figure 1A:
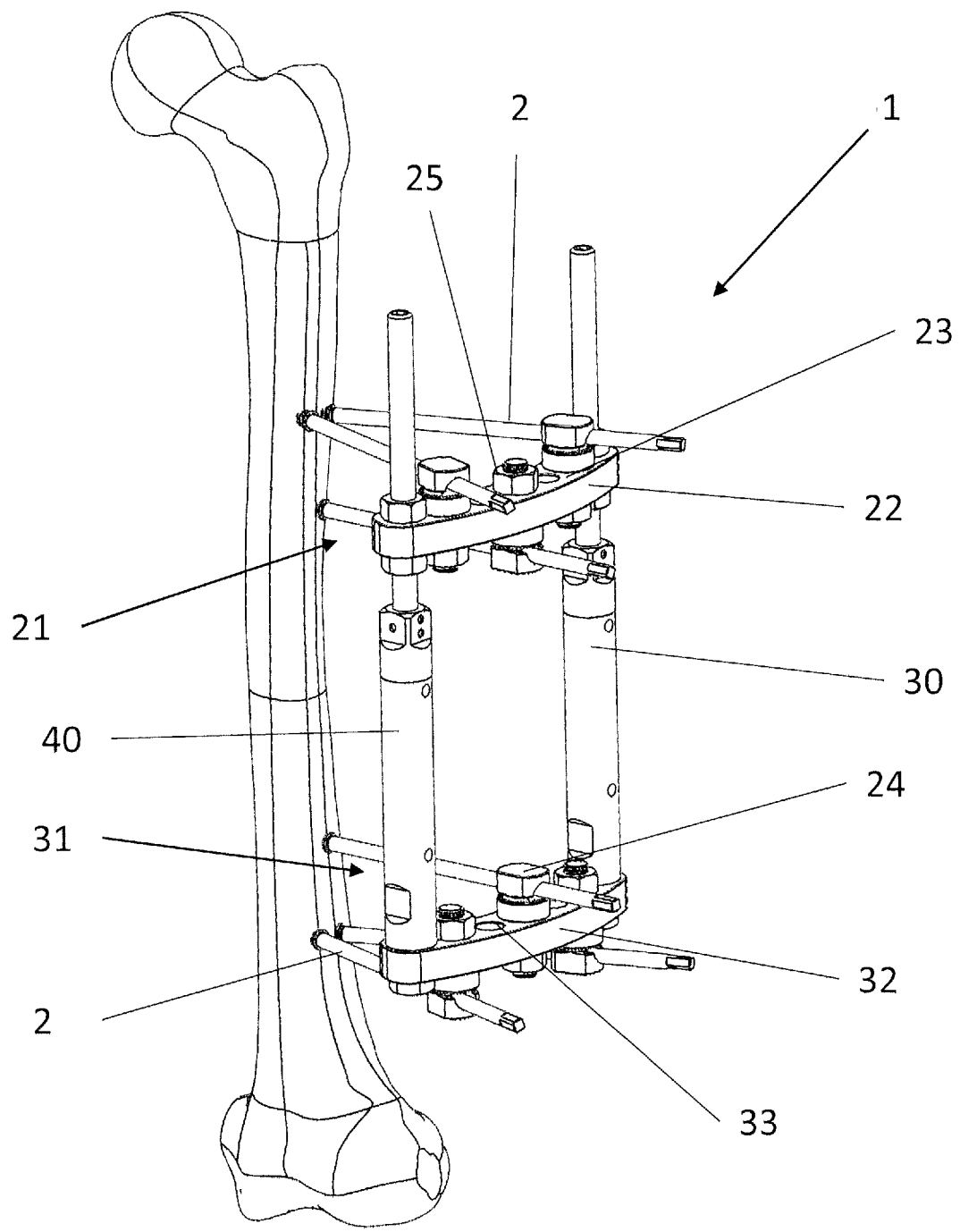
FIGS. 1A-1C show different views of an external modular fixation system according to the present invention for the temporary or permanent treatment of bone fractures of lower and upper limbs.
Figure 1B:
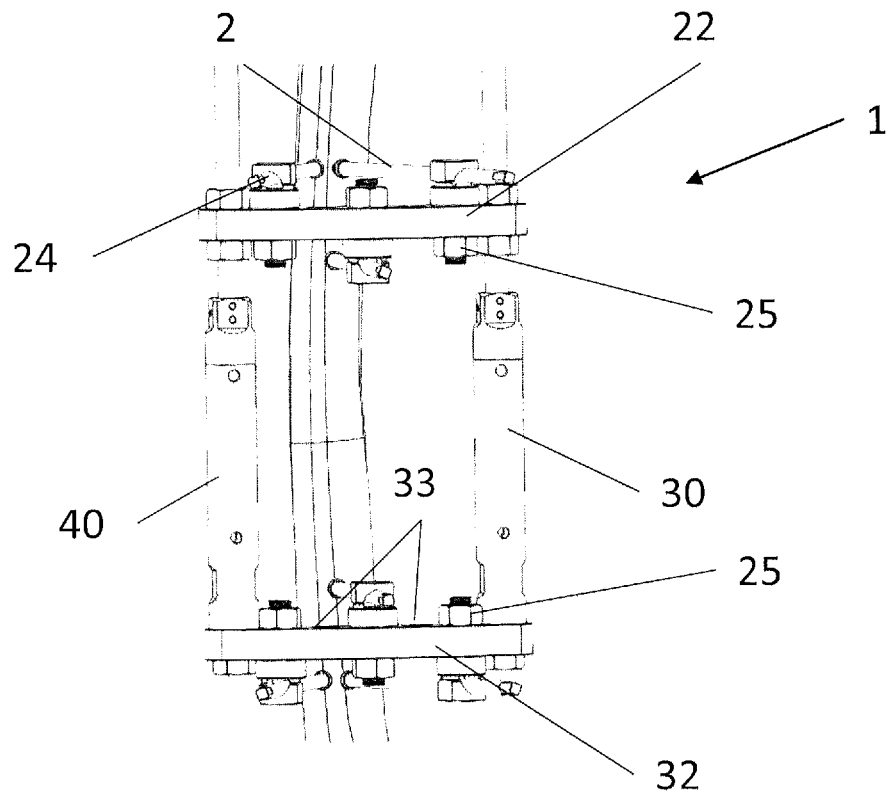
Figure 1C:
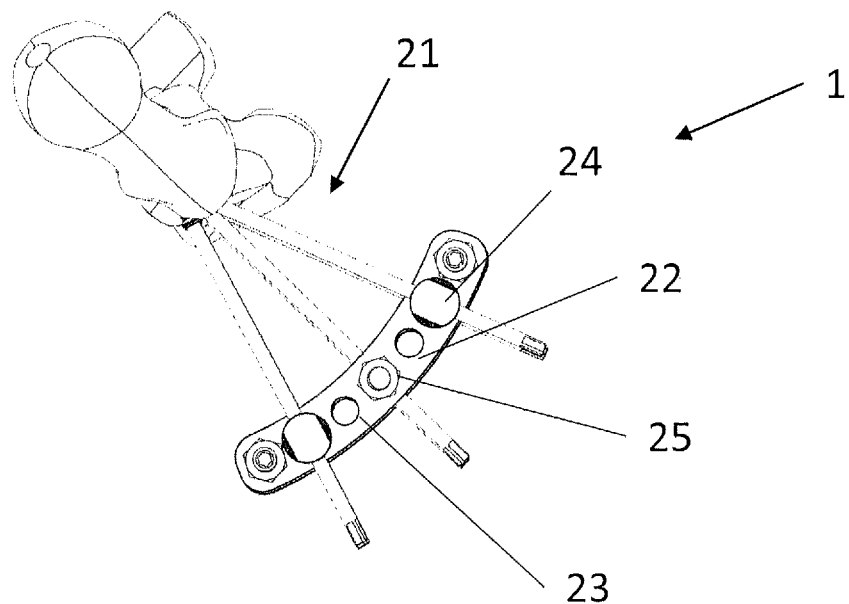

With reference to FIGS. 1A-1C, the reference number 1 globally and schematically indicates an external modular fixation system for the treatment of bone fractures and, more specifically, for temporary and/or permanent fixation applications in a method according to the present invention.

The modular system 1 includes a number of elongated pins or rods 2 having a particular structure. A modular clamp fixation device allows the pins 2 to be connected in a free and modular manner.

The elongated pin presents an elongated stem 3 extending along a longitudinal axis with an end portion 4 and a tip for insertion into a bone. The stem 3 is essentially cylindrical in shape although other shapes are possible.

The end portion 4 with tip has a conical shape with an external thread, forming a conical threaded end portion for insertion into the cortical portion of a bone.

In the following lines we will refer to this pin or rod 2 with the adjective monocortical to stress the fact that the threaded end portion 4 is inserted only into the cortical portion of the bone without penetrating into the medullary canal.

The profile of the opposite end 5 of the rod 2 is shaped to receive the engagement of a wrench or a spanner or for being inserted in a motor-driven torque-controlled drill.

Figure 7A:
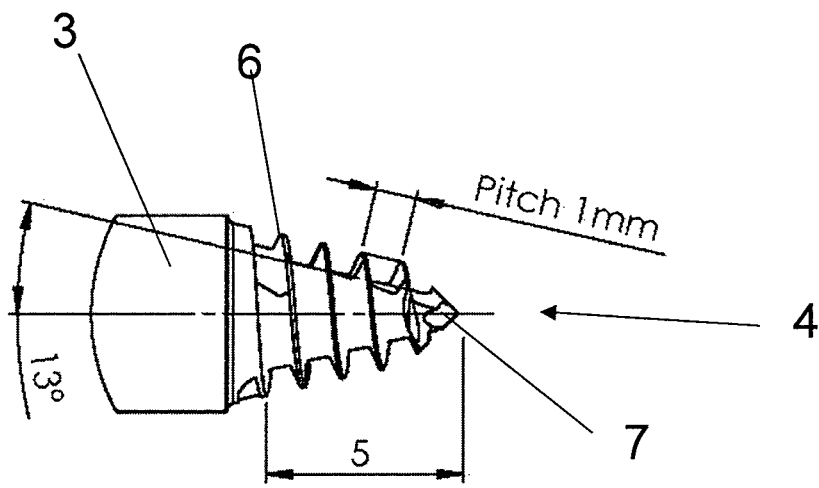
FIGS. 7A-7D show the thread profile of the threaded conical end portion of the elongated pin of FIG. 5 after the application of the thread.
Figure 7B:
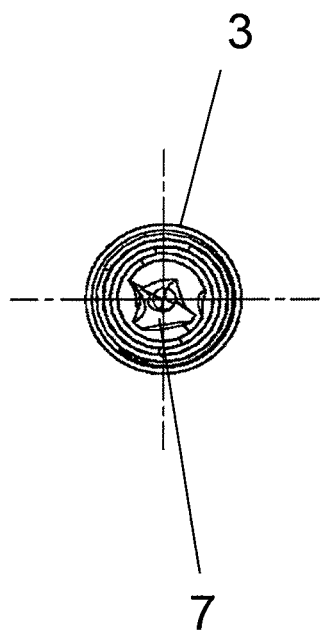
Figure 7C:
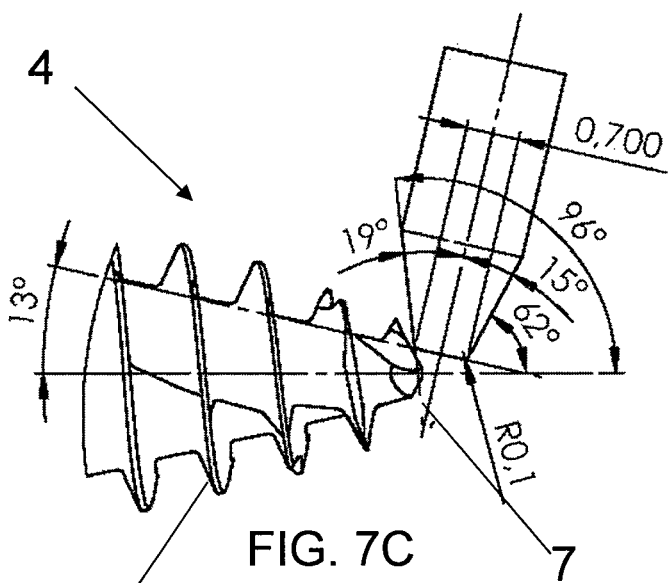
Figure 7D:
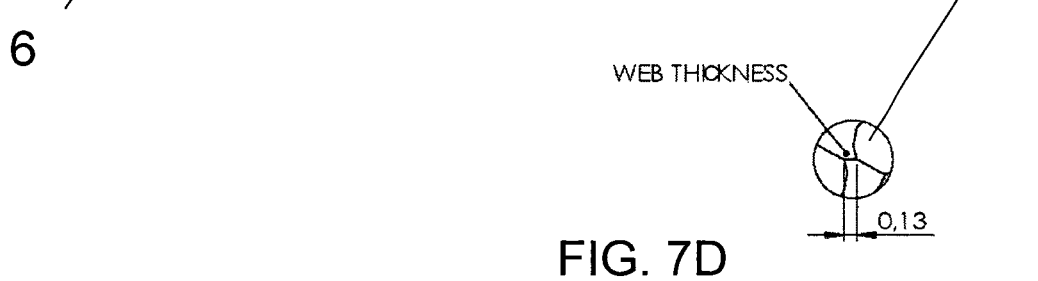

The threaded end portion 4 is shown in the enlarged view of FIG. 7A showing an embodiment in which the extension of the threaded conical end portion 4 along the longitudinal axis of the pin is equal to the diameter of the stem; this extension is specifically selected so that the conical end portion penetrates only the cortical portion of the bone.

The rod diameter may be between 3.5 mm and 6.0 mm according to the application. Preferred diameter sizes of the stem 3 of the pin are 4.0 mm and 5.0 mm, even if this value should not be considered as limiting the rights of the Applicant.

The length of the monocortical pin 2 may be from 80 mm to 160 mm, depending on the requirements of its particular application.

Figure 5:
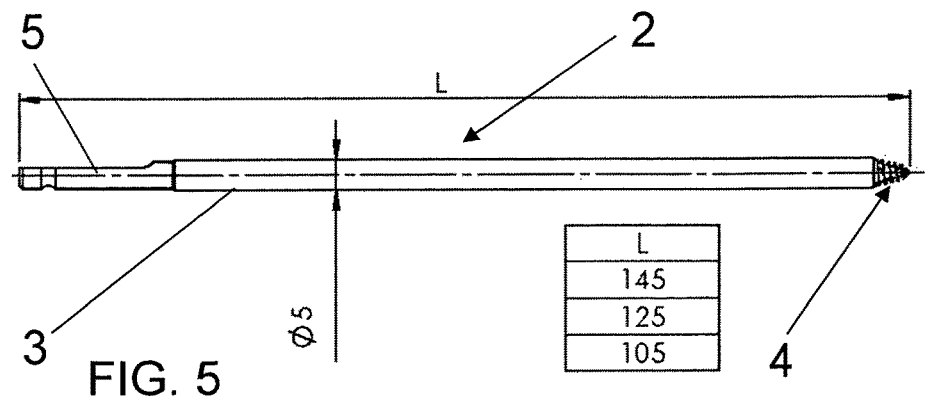
FIG. 5 is a view of an elongated pin according to a first embodiment for the external modular fixation system of the present invention.

With reference to the pin 2 shown in FIG. 5, the chosen length can be either 105 mm, 125 mm or 145 mm.

The stem 3 has a diameter of 5 mm. The length of the threaded conical end portion 4 taken along the longitudinal axis of the pin 2, shown in FIG. 7A, is equal to 5 mm, which means that the threaded end portion extends along a portion that is equal to the diameter of the stem 3.

A person skilled in the art may appreciate that the diameter combined with the length of the pin 2 will lend a particularly slender aspect to the pin.

Preferably the monocortical pin 2 is made of stainless steel with a relatively high elastic modulus that gives a predetermined rigidity to the stem 3 and, at the same time, a good resistance at the threaded end 4.

The threaded end portion 4 is:
self-drilling
self-cutting, and
self-tapping.

Hereinafter we will disclose a few specific and preferred values of the thread shape 6 and profile that are given as indicative examples of preferred measurements only, without any intention to limit the Applicant's rights.

The thread shape 6 has a helical profile and it is obtained at the tip end 4 of the monocortical pin or rod 2.

The conical end portion 4 has a drill-shaped point 7.

The conical angle of the threaded profile having a conical shape is set at 26°.

The threaded conical end portion 4 has an external diameter size of 1.9 mm at the tip.

Figure 6A:
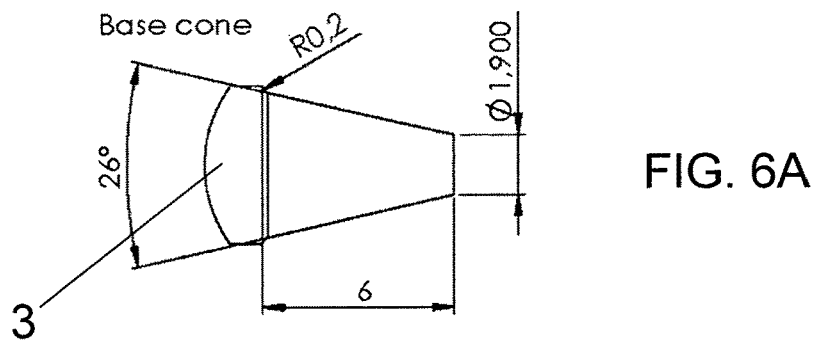
FIGS. 6A-6C show an enlargement of a conical end portion of the elongated pin of FIG. 5 before the application of the thread.
Figure 6B:
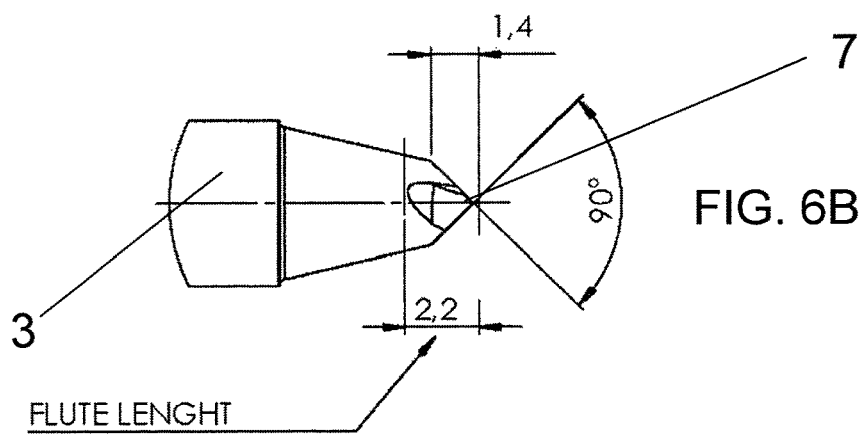
Figure 6C:
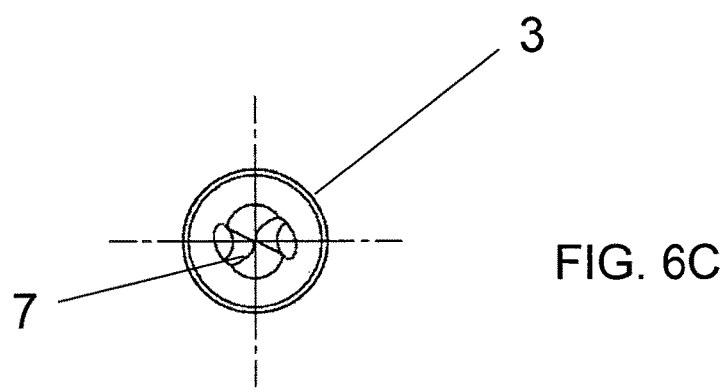

The drill-shaped point 7 has a point angle of about 85°-120°, preferably of 90°, as shown in FIG. 6B.

The tip of the conical end portion has a size of Ø 0.7 mm.

The thread pitch is equal to 1 mm.

The threaded end portion 4 has a total length of preferably 5.0 mm with an additional length of about 1.0 mm of the undercut, as shown in FIG. 7A. Therefore, the length of the thread end portion 4 is commensurate to the diameter of stem 3. The total number of threads is five.

In the embodiment of FIGS. 5-7D, the depth of thread of the helical profile is uniform along the conical end portion.

FIGS. 8-10D show an alternative embodiment of the threaded end portion 4 of the monocortical pin or rod 2.

The embodiment of FIGS. 8-10D differs from the embodiment of FIGS. 5-7D in that:
the diameter of the rod is equal to 4.0 mm
the number of threads is equal to four;
the depth of thread of the helical profile is not uniform along the conical end portion.

All measurements in many of the FIGS. 5-10D are given in mm., even where not explicitly indicated.

Figure 9A:
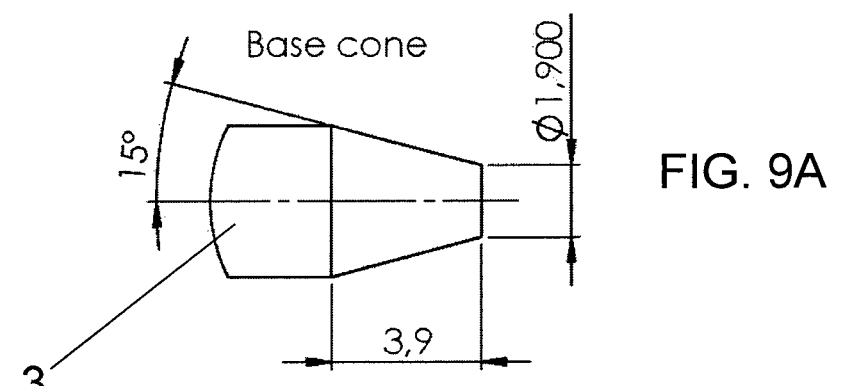
FIGS. 9A-9C show an enlargement of a conical end portion of the elongated pin of FIG. 8 before the application of the thread.
Figure 9B:
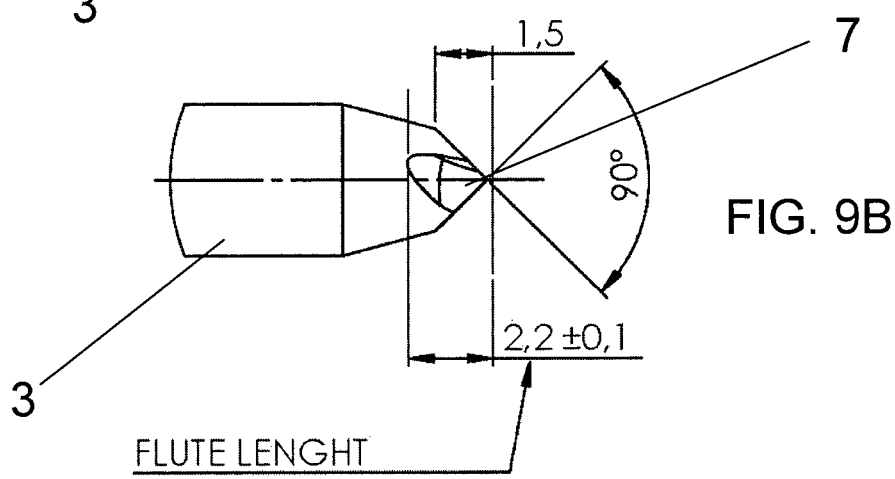
Figure 9C:
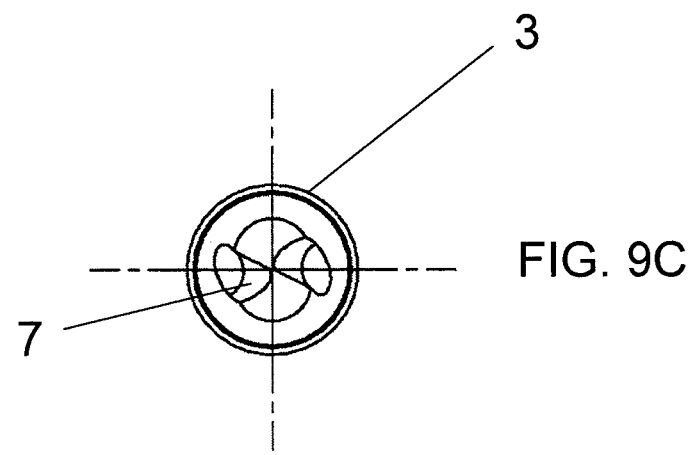
Figure 10A:
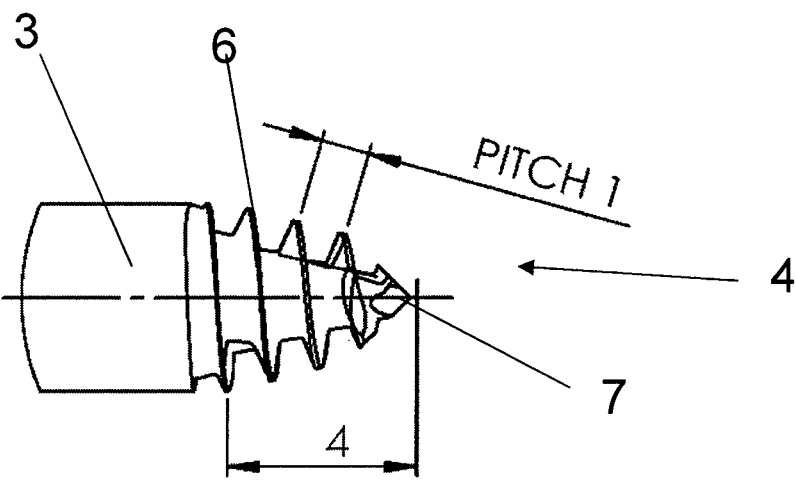
FIGS. 10A-10D show the thread profile of the threaded conical end portion of the elongated pin of FIG. 8 after the application of the thread.
Figure 10B:
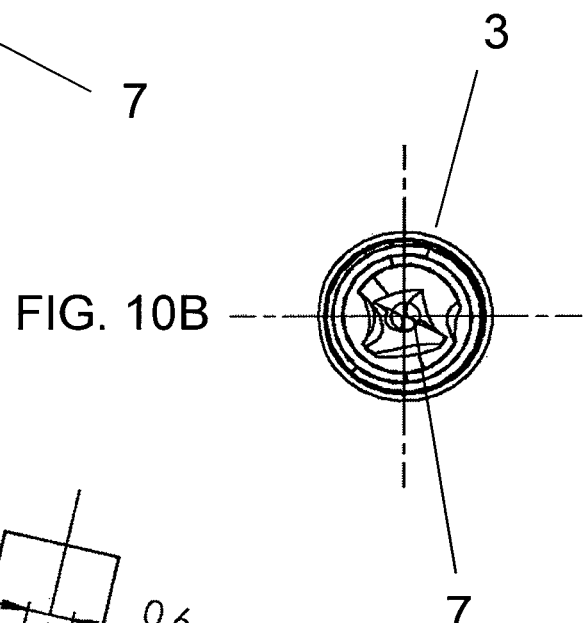
Figure 10C:
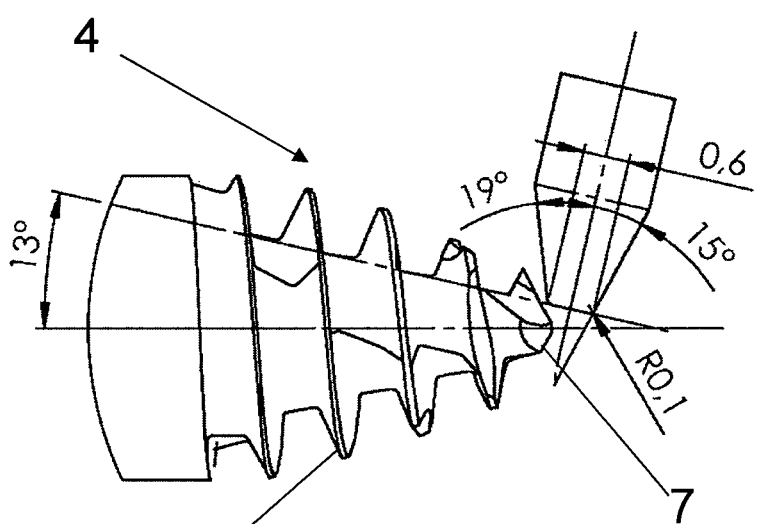
Figure 10D:
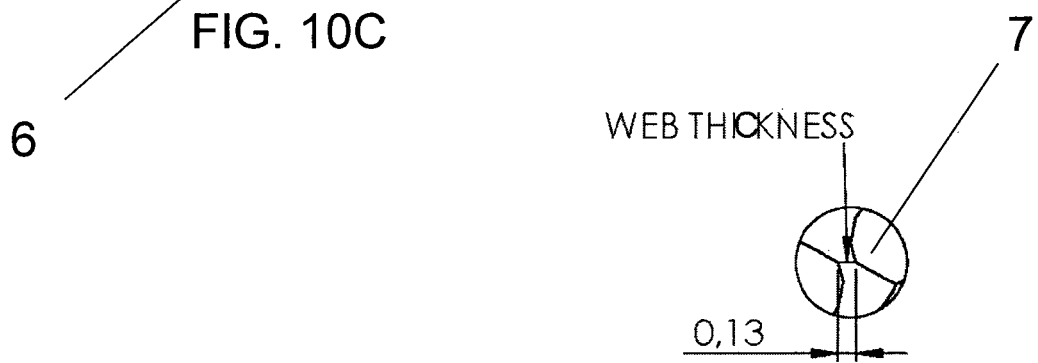

FIGS. 6A and 9A show a base cone of the distal conical end portion of the pin having diameters of 5 mm and 4 mm respectively; FIGS. 6B, 6C and 10B, 10C show the sharpening of the tip without thread of the distal conical end portion of the pin, with diameters of 5 mm and 4 mm respectively; FIGS. 7A-7D and 10A-10D show the finished tip with threaded distal conical end portion of the pin, with diameters of 5 mm and 4 mm respectively.

Figure 8:
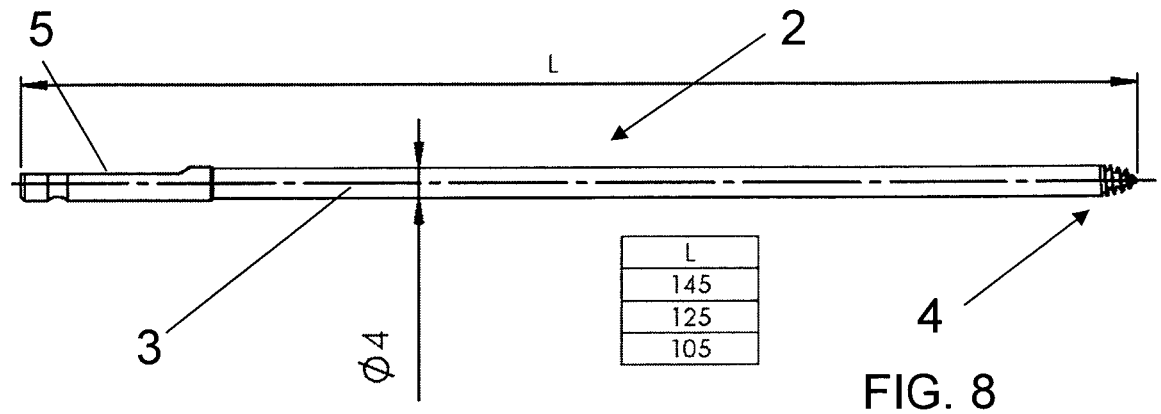
FIG. 8 is a view of an elongated pin according to a second embodiment of the external modular fixation system of the present invention.

The pin of FIG. 8 is particularly suited for pediatric applications, for instance in treatments for preadolescent children.

For adult applications it would be advisable to use a threaded end portion with a total length of 5 mm; in that case the diameter of the stem 3 may be 5 mm as well.

In any case, both embodiments of the pin disclosed here and shown in the enclosed figures share certain common features:
the ratio between the length of the threaded end portion 4 of the rod 2 and the diameter of the stem 3 is 1-1.2, preferably about 1;
the threaded end portion 4 presents self-drilling, self-cutting and self-tapping features.

The result of this selection provides for single thread profiles that are particularly thin and sharp, offering a large gripping surface during the penetration of the conical end portion into the cortical portion of the bone.

Testing by the Applicant provided surprising results in terms of high performance in the pull-out force applied to remove the pin 2 implanted in the cortical portion of a bone. The applied force was over 250 N for tests with low-density sawbones.

Moreover, during other tests performed with sawbones with a density of 50 PCF a pull-out force of about 484 N and a tightening torque of 0.95 Nm were measured, which is comparable to a regular screw implanted in the bone up to the medullary canal.

The pin of the present invention obtains a series of advantageous results listed below:

1) Pin less invasive for the skin;
2) Easy insertion without bone breakage;
3) Axial load of about 500 [N] (during bone lengthening with a nail in the medullary canal);
4) Simple structure means greater ease in bone distraction.

Now, with specific reference to FIGS. 1 to 4 an implementation of the pin 2 in the external modular fixation systems 1 and 10 of the present invention will be disclosed.

The external fixation systems 1 and 10 make use of two groups of pins 2, a proximal group 21 and a distal group 31.

The proximal group 21 includes at least three pins 2 that have their respective threaded conical ends inserted into the cortical bone portion at predetermined proximal distances from the bone fracture.

Similarly, the distal group 31 includes at least three pins 2 that have their respective threaded conical ends inserted into the cortical bone portion at predetermined distal distances from the bone fracture.

Figure 2:
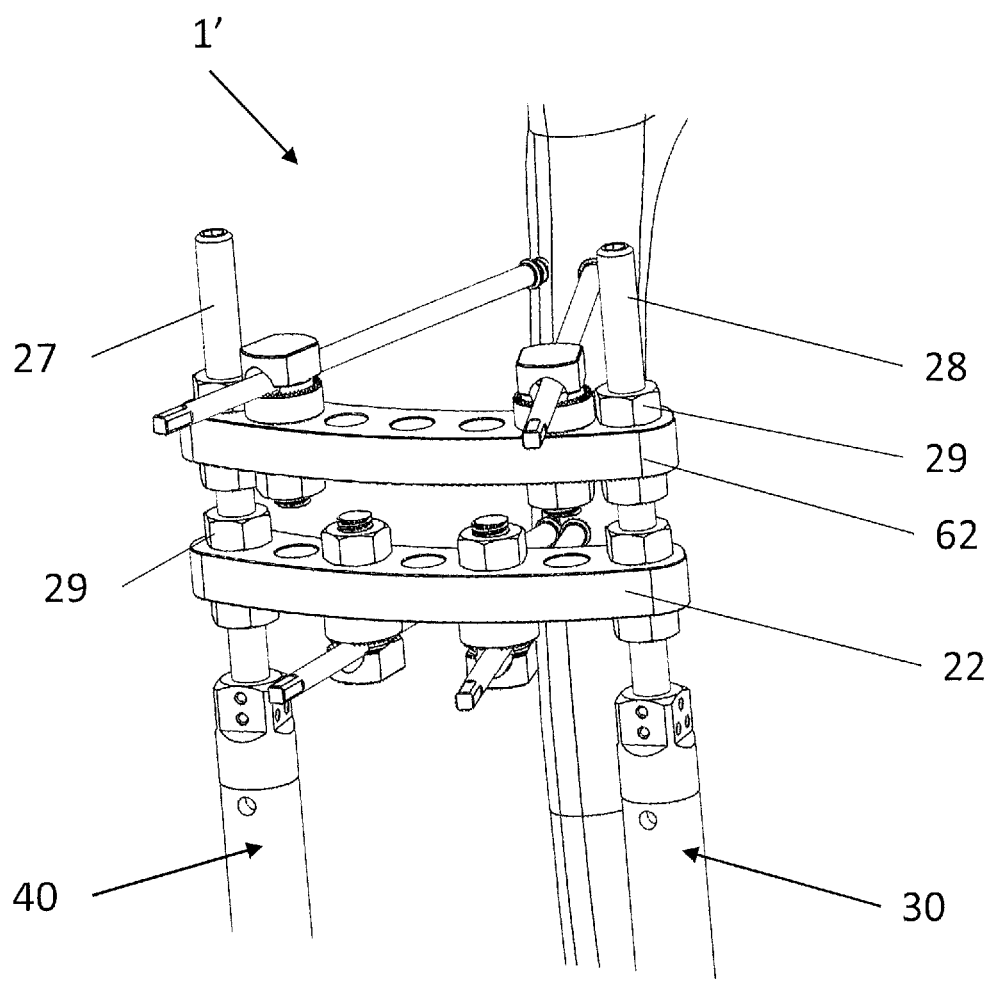
FIG. 2 shows a portion of an external modular fixation system presenting a minor constructional modification in comparison with the system of FIGS. 1A-1C.

Two of the three pins 2 of the proximal group 21 present respective converging longitudinal axes and may be considered to be on the same plane. This plane is parallel to the plane of a proximal clamp plate element 22. FIGS. 1A-1C show a proximal clamp plate element 22 and a distal clamp plate element 32. However, other clamp plate elements 62 can be used in a parallel fashion with respect to the proximal and distal plates 22 or 32 to improve the stability of the external modular fixator system of the present invention, as shown in the embodiment of FIG. 2 and as will become clear from the following paragraphs.

Each pin 2 of the proximal group 21 is supported by and fixed on the clamp plate element 22 at the free ends 5 of the pins that project toward the external part of the modular fixator 1.

The proximal clamp plate element 22 is substantially a plate with a predetermined thickness, rounded edges and a shape that is slightly curved like a circular segment, as shown clearly in FIG. 1C.

The plate 22 is provided with a number of holes 23, distributed regularly, to receive corresponding bolt 24 and nut 25 elements that fix the pin 2 to the plate 22.

The bolt 24 has a through-hole through which the pin 2 passes, which is then blocked in a stable position by tightening the nut 25.

Advantageously, a third pin 2 of the proximal group is also inserted in the cortical portion of the bone but extending with its longitudinal axis in a third direction that differs from the direction of the other two pins of the group of proximal pins. In this manner the three pins of the proximal group are not coplanar to each other.

More specifically, the third pin 2 is implanted with its threaded end portion 4 in an area of the cortical bone that is closer to the fracture than the position of the first two pins 2 of the proximal group 21 and fixed by a corresponding bolt 24 and nut 25 in a central position of the clamp plate 22.

This third pin is placed between the two other pins 2 of the proximal group 21. The other two pins 2 are fixed on the same side of the clamp plate 22 while the third pin in the middle is fixed to the other side of the clamp plate 22; together these three pins form the proximal group 21.

When an additional clamp plate element 62 is used to form a double clamp plate element, the proximal group is set up to include four pins 2 instead of three; two pins 2 are blocked on the first clamp plate element 22 and the other two pins 2 are blocked on the second clamp plate element 62, as shown for instance in FIG. 2.

When a couple of proximal clamp plate elements is used, the two proximal clamp elements 22 and 62 are placed in parallel and spaced apart by spacer rods 27 and 28 inserted into holes 23 at the extremities of both proximal clamp plate elements 22 and 62, where they are blocked by a respective nut 29.

The two pairs of pins fixed on each clamp plate element 22 and 62 may be positioned with different converging angles and may be fixed in different positions on the corresponding plates by means of nut and bolt couplings.

The same configuration with a couple of clamp plate elements can be provided at the distal position so that the distal group 31 may be arranged in a manner similar to the proximal group 21.

Two pins 2 of the distal group 31 have respective converging longitudinal axes and may be considered to be on the same plane. This plane is parallel to the plane of a clamp plate element 32. The FIGS. 1A-1C show both the proximal clamp plate element 22 and the distal clamp plate element 32 that are fixed in the fixator system 1 in parallel fashion.

The proximal and distal groups 21 and 31 are mounted on the external modular fixation system of the present invention by spacer rods 30 and 40 which extend parallel to each other and which are attached to the extremities of the clamp plate elements 22 and 32.

These spacer rods 30, 40 may comprise a respective dynamic distractor element to allow the distance between the proximal group 21 and the distal group to be adjusted as desired, which would permit the fixator system 1 to be used also for limb lengthening applications, as will be explained later.

Each pin 2 of the distal group 31 is supported by and fixed on the clamp plate element 32 in the proximity of the free ends 5 of the pins that project toward the external part of the modular fixator 1.

The distal clamp plate element 32 is structurally identical to the proximal clamp plate element 22; it is a plate with a predetermined thickness and a shape that is slightly curved like a circular segment.

The distal clamp plate element 32 is also provided with a number of holes 33, distributed regularly, to receive corresponding bolt 24 and nut 25 elements to fix the pin 2 to the plate 32.

Each bolt 24 has a through-hole through which a corresponding pin 2 passes that is then blocked in a stable position by tightening the nut 25.

Advantageously, a third pin 2 of the distal group is also inserted in the cortical portion of the bone but extending with its longitudinal axis in a third direction that differs from the direction of the other two pins of the group of distal pins. In this manner the three pins of the distal group are not coplanar to each other.

More specifically, the third pin 2 is implanted with its threaded end portion 4 in an area of the cortical bone that is closer to the fracture than the position of the first two pins 2 of the distal group 31 and fixed by a corresponding bolt 24 and nut 25 in a central position of the clamp plate 32.

This third pin is placed between the two other pins 2 of the distal group 31. The other two pins 2 are fixed on the same side of the clamp plate 32 while the third pin in the middle is fixed to the other side of the clamp plate 22; together these three pins form the distal group 31.

When an additional clamp plate element 62 is used to form a double clamp plate element, the distal group is set up to include four pins 2 instead of three; two pins 2 are blocked on the first clamp plate element 22 and the other two pins 2 are blocked on the second clamp plate element 62.

When a couple of distal clamp plate elements is used, the two distal clamp elements 22 and 62 are placed in parallel and spaced apart by spacer rods 27 and 28 inserted into holes 23 at the extremities of both distal clamp plate elements 22 and 62, where they are blocked by a respective nut 29.

The two pairs of pins fixed on each clamp plate element 22 and 62 may be positioned with different converging angles and may be fixed in different positions on the corresponding plates by means of nut and bolt couplings.

Figure 3:
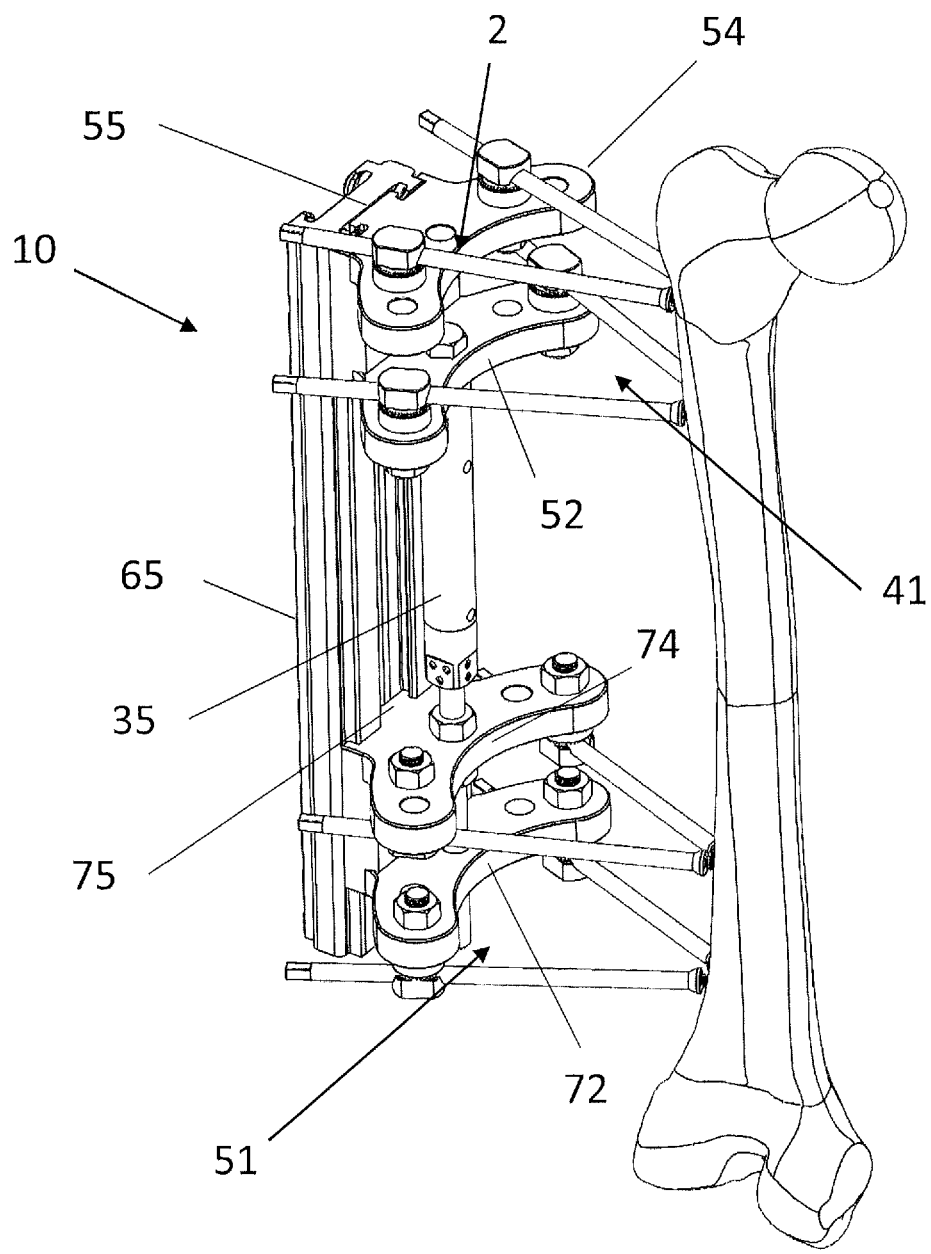
FIG. 3 is a perspective view of an external modular fixation system according to a different embodiment of the present invention.

With reference to the other embodiment of the external modular fixation system 10 of the present invention, shown in FIG. 3, it represents a customized version of the embodiments shown in FIGS. 1A-1C and 2.

In this embodiment the proximal and distal clamp plate elements are identified by the numerals 52 and 72 respectively, because their structure is slightly different from the structure of the clamp plate elements 22 and 32 of the first embodiment.

More specifically, these clamp plate elements 52 and 72 are also shaped like a circular segment. They have a respective central projecting portion 55, 75 which projects in a direction away from the bone, and they are slidably mounted on a common fixation rod 65.

Advantageously, each central projecting portion 55, 75 may be integrally formed with a couple of parallel proximal clamp plate elements 52, 54 of the proximal group 41 and with a couple of parallel distal clamp plate elements 72, 74 of the distal group 51 respectively, thus forming a proximal clamp body consisting of a single piece comprising the couple of parallel proximal clamp plate elements 52, 54 and the central projecting portion 55 and a distal clamp body consisting of a single piece comprising the couple of parallel distal clamp plate elements 72, 74 and the central projecting portion 75.

The manner of supporting the pins 2 with bolt and nut couplings is substantially identical to the embodiment previously disclosed.

Advantageously, the central projecting portion 55, 75 confers a particular rigidity to the proximal clamp body and to the distal clamp body. Each central projecting portion 55, 75 may be shaped as a slide to be supported by fixation rod 65, as clearly shown in the example of FIG. 3.

The embodiment of FIG. 3 allows the use of a single distraction element 35 that is placed parallel to said fixation rod 65 for the dynamic distraction between the proximal and distal clamp body.

Figure 4:
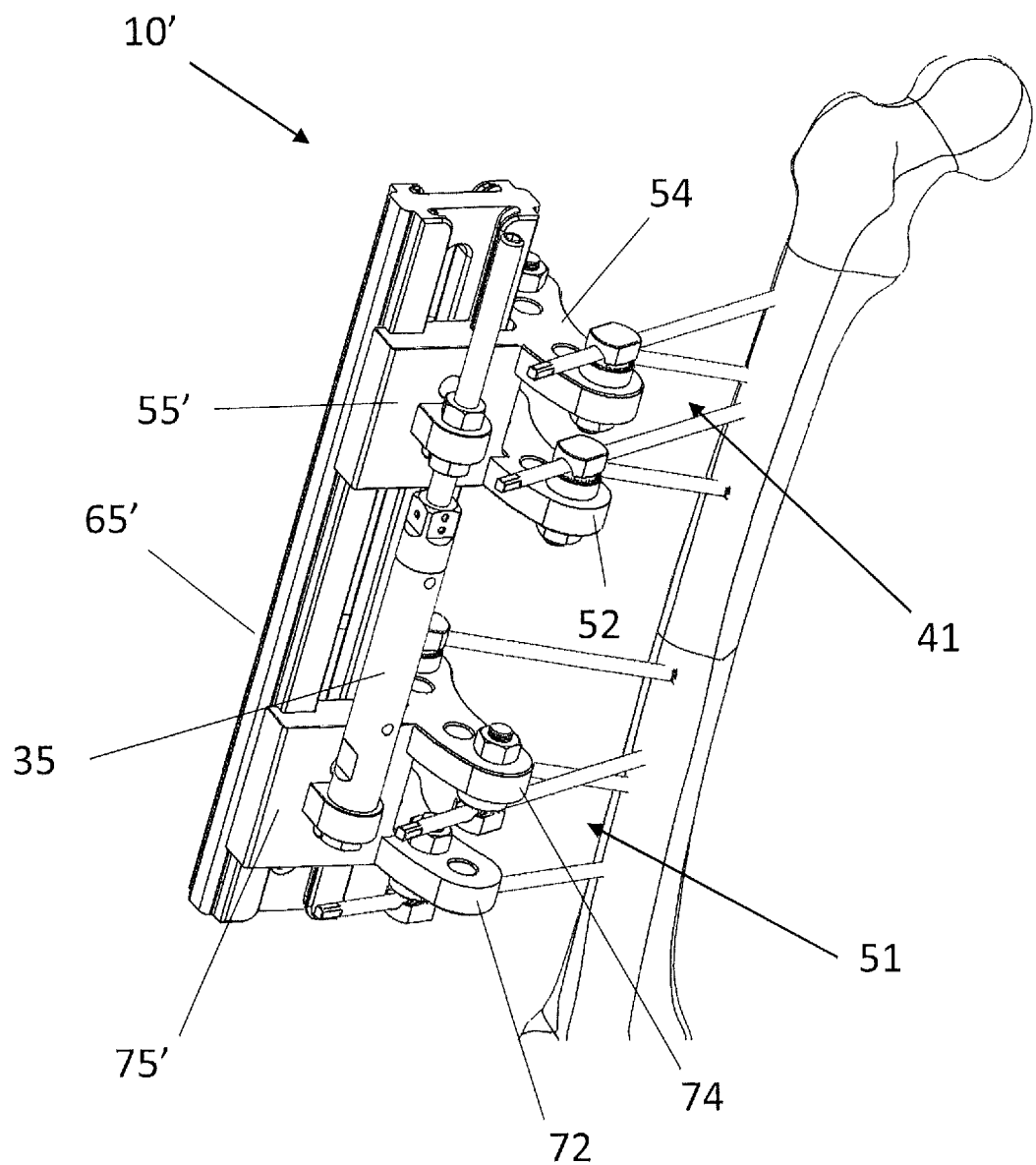
FIG. 4 is a perspective view of an external modular fixation system presenting a minor constructional modification with respect to the system of FIG. 3.

FIG. 4 shows an external modular fixation system 10' very similar to the embodiment of FIG. 3. Here the central projecting portions 55', 75' project for a portion that is greater than the projecting portion of the embodiment illustrated in FIG. 3. These much longer projecting portions 55', 75' are slidably mounted on a common rail rod 65'. The distraction element 35 is directly fixed to the central projecting portions 55', 75'.

Of the utmost importance in the modular fixation system of the present invention is the fact that the fixing clamp blocks three of the elongated pins in a fixed position with their longitudinal axes not coplanar with each other.

Thanks to this particular arrangement the group of three pins on different planes forms a hyperstatic structure.

The modular fixation system of the present invention may be employed in a technique of femoral or tibial lengthening over an intramedullary nail for applications in both children and adults, as disclosed hereafter.

As a matter of fact the present invention allows for the implementation of a new technique for tibial or femoral lengthening simultaneously using or combining the modular external fixator 1, 1' or 10, 10' of the present invention together with an intramedullary nail.

The external fixator 1, 1' or 10, 10' and the intramedullary nail are applied together at the moment of osteotomy.

Used in combination with the modular fixation system of the invention, this technique improves alignment and shortens the time with respect to using traditional external fixation devices using pins that penetrate into the medullary canal.

A nail is inserted into the medullary cavity of the bone while the external fixator of the present invention is fixed only to the cortical portion of the bone.

The lengthening phase by callotasis is performed with the external fixator system of the present invention.

In this manner it is possible to control callus formation according to lengthening speed and physiological requirements.

Once the lengthening phase is completed, the nail is blocked by distal screws while the external fixator is removed during the phase of callus consolidation that normally takes three months.

Therefore the time in which the external fixator is applied is reduced by more than half when compared with prior art solutions.

It should be considered that an external fixator is generally not readily accepted, especially by children.

Possible problems of angular deviations during the lengthening phase with the external fixator mounted, are greatly reduced with the system of the present invention, as the lengthening is guided inside the medullary canal by the presence of the nail.

Therefore, according to the invention, the basic idea is that of dividing the treatment into different phases while keeping the nail inside the medullary canal in-between the two treatment phases.

To avoid any contact with screws normally used in traditional external fixation, the invention involves just the elongated pins 2 that are driven into only the first cortical portion of the bone without penetrating into the medullary canal, which consequently remains free to receive the nail.

Also the diameter of the pins 2 is important to avoid skin problems. Therefore the reduced dimension of the threaded end portion 4 and the pin stem 3 create fewer complications and greater acceptance of the external fixation system by patients.

The number and positioning of the pins 2 in a sort of triangular configuration both at the proximal and the distal portions of the fixator is a guarantee of a strong fixation of the whole fixator structure.

In essence the pins 2 are implanted only in the cortical bone portion and they do not penetrate the medullary canal, thereby avoiding any risk of infection as there is no contact between the nail and the external fixation pins.

Therefore thanks to this invention this technique can even be implemented in tibial lengthening over nails for children, which will overcome all counter-indications and risks of causing growth arrest through serious infection.

As the limb is lengthened, one end of the bone slides over the nail and the new bone is grown around it.

The lengthening of the bone may be followed by a corresponding distraction of the modular fixation system.

After the bone is lengthened, the patient returns to the operating room for the insertion of special screws that lock the nail to the bone. The screws are generally positioned at both ends of the nail on opposite sides of the lengthening zone.

The external fixation system may then be removed during the same operation.

Among other advantages, this approach eliminates the risk of pin infection and muscle tethering by the pins, and causes less pain and discomfort.

This process shortens the total treatment time with an external fixator by more than half. However, tibia or femur lengthening over nails may not be appropriate for all patients, particularly for patients whose problem is linked to an infection, or for young children.

The invention claimed is:

1. An external modular fixation system for temporary and/or permanent fixation applications to treat bone fractures and to connect two or more bone fragments to each other, comprising at least three identical elongated pins, each pin comprising an elongated stem extending along a longitudinal axis with a first end portion and an opposite second end portion, each elongated stem being cylindrical in shape and having an unthreaded lateral outer surface, said first end portion comprising a tip having a conical shape with an external thread, forming a conical threaded end portion, wherein the conical threaded end portion is self-drilling, self-cutting and self-tapping, wherein a ratio between an axial length along the longitudinal axis of the conical threaded end portion of the elongated pin and a diameter of the unthreaded lateral outer surface of the elongated stem is 1-1.2, specifically selected so that the conical threaded end portion penetrates only a cortical portion of a bone.

2. The external modular fixation system according to claim 1, comprising a first fixation clamp element blocking three of said elongated pins in a fixed position, said three pins being blocked in their respective positions with their longitudinal axes not coplanar to each other.

3. The external modular fixation system according to claim 2, comprising a second fixation clamp element blocking three further elongated pins in a fixed position, said three further pins being blocked in their respective positions with their longitudinal axes not coplanar to each other, the first and second fixation clamp being connected to each other by spacer rods to form a single rigid structure.

4. The external modular fixation system according to claim 3, wherein said first and second clamp elements comprise respectively first and second plate elements of a predetermined thickness and slightly curved like a circular segment.

5. The external modular fixation system according to claim 4, wherein said first and second clamp plate elements are provided with a number of holes, regularly distributed, for receiving corresponding bolt and nut elements to attach the elongated pins to the first and second clamp plate elements.

6. The external modular fixation system according to claim 5, wherein said first and second clamp plate elements comprise a central projecting portion to be connected to a common fixation rod.

7. The external modular fixation system according to claim 6, wherein said central projecting portion is integrally formed with two parallel clamp plate elements.

8. The external modular fixation system according to claim 7, wherein said central projecting portion is slidably mounted on a rail rod that connects said first and second clamp elements.

9. The external modular fixation system according to claim 8, wherein a distraction element is directly fixed to the central projecting portions.

* * * * *